United States Patent [19]

Gasper et al.

[11] Patent Number: 4,968,542
[45] Date of Patent: * Nov. 6, 1990

[54] CURABLE MATERIAL FOR SEMI-RIGID RESILIENT ORTHOPEDIC SUPPORT

[75] Inventors: Alton J. Gasper, Minneapolis; Dennis C. Bartizal, Woodbury, both of Minn.

[73] Assignee: Minnesota Mining and Manufacturing Company, St. Paul, Minn.

[ * ] Notice: The portion of the term of this patent subsequent to Jan. 16, 2007 has been disclaimed.

[21] Appl. No.: 903,281

[22] Filed: Sep. 3, 1986

[51] Int. Cl.$^5$ ................................................ A61F 5/04
[52] U.S. Cl. ......................................... 428/76; 128/90; 206/389; 206/438; 206/440; 428/254; 428/255; 428/272; 428/273; 428/307.3; 428/308.4; 428/311.5; 428/423.5; 428/423.7; 428/424.4; 428/424.8; 428/425.6; 428/542.8; 428/913
[58] Field of Search .................... 128/89 R, 90, 91 R; 428/251, 253, 352, 425.6, 913, 76, 254, 255, 272, 273, 542.8; 206/389, 438, 440

[56] References Cited

U.S. PATENT DOCUMENTS

| | | | |
|---|---|---|---|
| 2,650,212 | 8/1953 | Windemuth | 260/75 |
| 3,373,741 | 3/1968 | Hill et al. | 128/90 |
| 3,763,858 | 10/1973 | Buese | 128/156 |
| 3,847,722 | 11/1974 | Kistner . | |
| 3,874,376 | 4/1975 | Dart et al. | 128/90 |
| 3,882,857 | 5/1975 | Woodall, Jr. | 128/90 |
| 4,134,397 | 1/1979 | Gianakakos et al. | 128/90 |
| 4,235,228 | 11/1980 | Gaylord, Jr. et al. | 128/91 |
| 4,315,703 | 2/1982 | Gasper | 405/264 |
| 4,376,438 | 3/1983 | Straube et al. | 128/90 |
| 4,411,262 | 10/1983 | von Bonin et al. | 128/90 |
| 4,427,003 | 1/1984 | Fennimore et al. | 128/90 |
| 4,433,680 | 2/1984 | Yoon | 128/90 |
| 4,442,833 | 4/1984 | Dahlen et al. | 128/90 |
| 4,502,479 | 3/1985 | Garwood et al. | 128/90 |
| 4,519,856 | 5/1985 | Lazzara . | |
| 4,598,826 | 7/1986 | Shinbach | 206/620 |
| 4,609,578 | 9/1986 | Reed | 428/76 |
| 4,667,661 | 5/1987 | Scholz et al. | 128/90 |
| 4,705,840 | 11/1987 | Buckanin | 528/53 |
| 4,893,617 | 1/1990 | Bartizal et al. | 128/90 |

FOREIGN PATENT DOCUMENTS 1979100181 8/1979 Japan ............................ 94 A/237

OTHER PUBLICATIONS

"Cast Tips–Silicone (Sports) Cast Application", C. Henderson, *Online Communications,* a publication of the National Association of Orthopedic Technologists, vol. 4, No. 6, Nov./Dec. 1986.

Electro Insulation Corporation product information and letter from same.

"The Modified Silicone Rubber Playing Cast", J. A. Bradley, *The Physician and Sportsmedicine,* vol. 10, No. 11, Nov. 1982.

"Soft Playing Splint for Protection of Significant Hand and Wrist Injuries in Sports", J. A. Bergfeld et al., from the *48th Annual Meeting of the American Academy of Orthopedic Surgeons,* Las Vegas, Nev., Feb. 1981.

*Primary Examiner*—James C. Cannon
*Attorney, Agent, or Firm*—Donald M. Sell; Walter N. Kirn; Dale E. Hulse

[57] ABSTRACT

A curable orthopedic support material is disclosed comprising a flexible sheet material impregnated with a liquid resin system which cures upon exposure to a curing agent to a resilient, semi-rigid support device. The cured support is especially designed for orthopedic applications where conventional rigid casts are not desirable and/or necessary.

23 Claims, No Drawings

CURABLE MATERIAL FOR SEMI-RIGID RESILIENT ORTHOPEDIC SUPPORT

FIELD OF THE INVENTION

This invention relates broadly to the field of orthopedic support devices, including casts and splints and materials for their fabrication. It also relates to non-rigid supports such as elastic bandages and wraps.

BACKGROUND ART

Severe injury to body limbs, particularly injuries involving a fracture of the bone, are typically treated by immobilizing the injured limb in a rigid cast. Prior to about 1980, the vast majority of such rigid casts were made of plaster-of-paris. Since about 1980, synthetic casting materials, particularly those comprising a knitted fiberglass fabric impregnated with a water-activated polyurethane prepolymer resin system, have become quite popular. These polyurethane casting materials, like plaster-of-paris bandages, are dipped in water, then wrapped around the injured limb or body part and shaped while the material is soft and pliable. The resin cures into a rigid immobilizing cast within a few minutes after application to the body.

Polyurethane casts offer numerous advantages over plaster-of-paris, including a high strength-to-weight ratio, porosity, improved radiolucency and water resistance. Because of these advantages, they are generally preferred, even though they are significantly more expensive than plaster-of-paris.

Plaster-of-paris casts and known polyurethane casts, because of their rigidity, are not suitable for treating injuries where total immobilization is not necessary and/or desirable, as for example, in the case of strains, sprains, and some minor fractures.

These injuries are typically treated with a flexible-type support such as tape or an elastic bandage, e.g., an "Ace" bandage, which is not impregnated with a hardening agent. Such supports offer various degrees of immobilization, and the support they provide is not necessarily stable and constant over time.

It has been discovered that a need exists for a cured, custom-fitted resilient support device which offers the stability of a cured cast without the rigidity and degree of immobilization attendant with currently available casting materials.

SUMMARY OF THE INVENTION

The present invention provides a curable orthopedic support material comprising: a flexible sheet material impregnated with a liquid resin system which cures upon exposure to a curing agent into a semi-rigid, resilient support device having an "Immobilization Value" between 50 and 400 pounds and a "Resiliency Value" of at least 80 percent in the tests described hereinbelow. The support material further comprises packaging means for preventing contact of the resin with the curing agent prior to use. The invention also relates to the method of applying the support material and to the cured device formed from the support material.

In the preferred embodiment of the support material, a stretchy, knitted fabric, preferably polyester or fiberglass, is impregnated with a moisture-curing polyurethane prepolymer resin system wherein the theoretical isocyanate equivalent weight of the prepolymer is between about 500 and 5000 grams, the NCO/OH ratio is between about 1.5 and 5.0, and the average hydroxy equivalent weight of the polyol is at least 400, and preferably at least 1000 grams. The material is stored prior to use in a moisture impervious package such as that described in U.S. Pat. No. 4,598,826.

The curd support device provides stable semi-rigid support to the limb, allows some degree of movement, and has the ability to resume its original shape after deformation. It can be easily removed by cutting with a scissors, or if the device is formed by wrapping a resin-impregnated tape around the limb, the support device can be removed by unwrapping.

The support materials of the invention are useful in a variety of orthopedic applications in both humans and animals, particularly as a semi-rigid support for sprains and minor fractures, or as a protective device to prevent injury. Both of these applications are especially useful in the field of sports medicine. The support material may also be used as a secondary cast after primary healing of a fracture has occurred. Other applications include cast bracing where immobilization of the fracture area is required but movement in the proximate joint such as elbow, knee, or ankle is desired.

DETAILED DESCRIPTION

The most preferred resins for use in the support materials of the present invention are moisture-curing polyurethane prepolymers prepared by the reaction of a polyol with an excess of polyisocyanate. The starting materials are from the same chemical classes as those used to form the rigid polyurethane casting materials well known in the art as described in U.S. Pat. Nos. 4,376,438, 4,433,680 and 4,502,479. However, the isocyanate equivalent weights of the prepolymers and the average hydroxy equivalent weight of the polyol must be modified to obtain the semi-rigid properties of the support materials of the present invention.

Additionally, other active hydrogen materials may be used alone or in conjunction with polyols to produce polymers which will be useful in this invention. Examples are primary and secondary amines, carboxylic acids and thiols. When materials such as these are used, the overall equivalent weight of the active hydrogen components should be at least 400 grams and preferably at least 1000 grams.

Suitable isocyanates are disclosed in the aforementioned patents. Those which are preferred include 2,4'-diphenylmethane diisocyanate, 4,4'-diphenylmethane diisocyanate, mixtures of these isomers together with possible small quantities of 2,2'-diphenylmethane diisocyanate (typical of commercially available diphenylmethane diisocyanate), and aromatic polyisocyanates and their mixtures such as are derived from phosgenation of the condensation product of aniline and formaldehyde. It is preferred to use an isocyanate which has low volatility such as diphenylmethane diisocyanate rather than a more volatile material such as toluene diisocyanate.

The degree of rigidity and resiliency in the cured support device is generally determined by the average hydroxy equivalent weight of the polyol or polyol blend. In general, the average hydroxy equivalent weight of the polyol or polyol blend will be greater than about 400 grams and preferably greater than 1000 grams in order to achieve the desired degree of semi-rigidity and resiliency. The choice of hydroxy equivalent weight is also dependent upon the molecular structure and type of the isocyanate as is well known. Suitable commercially available isocyanate starting materials include "Isonate" 143L (Dow Chemical), "Mondur" MRS (Mobay), and "PAPI" (Dow Chemical).

Typical polyols for use in the prepolymer resin system include polyalkylene ethers derived from the condensation of alkylene oxides (such as those available from Union Carbide under the tradename "Niax" and from BASF Wyandotte under the tradename "Pluracol"), polytetramethylene ether glycols (such as "Polymeg" from the Quaker Oats Co.), polycaprolactone polyols (such as "Niax" PCP series of polyols from Union Carbide), and polyester polyols (hydroxyl-terminated polyesters obtained from esterification of dicarboxylic acids and diols) such as the "Rucoflex" polyols available from Ruco division, Hooker Chemicals Co.).

An especially preferred resin for use in the support materials of the invention uses an isocyanate known as "Isonate" 143L available from Dow Chemical (a mixture of isocyanate compounds containing about 73% by weight of diphenylmethane diisocyanate) and a mixture of polypropylene oxide polyols available from Union Carbide as "Niax" LHT-28 and PPG 425. To prolong the shelf-life of the material, it is preferred to include about 0.02–0.1 percent by weight of benzoyl chloride and/or other suitable stabilizer (e.g., an antioxidant such as butylated hydroxy toluene at a level of about 0.05 to 0.25 weight percent).

Foaming of the resin which reduces the porosity of the cured device and its overall strength should be minimized. Foaming occurs because carbon dioxide is released when water reacts with isocyanate groups.

The most satisfactory method of minimizing foaming involves the addition of a foam suppressor such as silicone Antifoam A (Dow Corning), DB-100 silicone fluid (Dow Corning), or silicone surfactants L550 or L5303 (Union Carbide) to the resin. It is preferred to use a silicone liquid such as Dow Corning DB-100 at a concentration of about 0.1 to 1.0 percent by weight.

The isocyanates and the polyols are reacted with one another under conventional polyurethane reaction conditions known to those skilled in the art. The NCO:OH ratio of the reactants is in the range of about 1.5:1 to 5.0:1 and preferably between 2.5:1 and 3.4:1. The theoretical isocyanate equivalent weight of the prepolymer should be in the range of 500 to 5000 grams, preferably between 800 and 1200 grams with the average hydroxy equivalent weight of the polyol being at least 400 grams preferably at least 1000 grams.

Other water-activated and alternative curing resins may be used to produce the curable support materials of the invention such as moisture-curing polyurea prepolymers, silane, epoxy, acrylate, polysulfide and polyester functional materials. Light-curing materials such as certain active olefins, e.g., arcylates, allylics and pendant vinyls, are also candidates.

The resins used in the support materials of the invention tend to be more sticky than those used to form rigid casts. In order to improve handling characteristics, it is preferred to reduce the tack in accordance with one or more of the methods described in U.S. Pat. Nos. 4,667,661 and 4,794,937. The preferred method of detackifying the polyurethane prepolymer resin systems involves the addition of a lubricant, especially a surfactant, to the system. The preferred surfactants are block copolymers of propylene oxide and ethylene oxide in an amount ranging from 3 to 6 percent by weight of the prepolymer system. Especially preferred are hydroxy functional polyethylene oxide terminated polyproylene oxides (sold under the tradename "Pluronic" by BASF Wyandotte).

The resin also preferably contains a catalyst to control the set time of the resin. To produce the cured support devices of the present invention, a cure time of about 3–18 minutes, preferably 4–10 minutes following exposure to the curing agent, e.g., dipping in water, is preferred.

Suitable catalysts for moisture-curing polyisocyanate prepolymer resin systems are well known. Tertiary amine catalysts such as 2,2'-dimorpholinodiethyl ether (DMDEE) described in U.S. Pat. No. 4,433,580 and 4-[2-[1-methyl-2-(4-morpholinyl)-ethoxy]ethyl]-morpholine (MEMPE) described in copending application Ser. No. 784,344 filed Oct. 4, 1985, in amounts ranging from 1 to 3 percent by weight of the resin system are especially preferred.

The flexible sheet material used in the support material of the present invention is preferably porous such that the sheet is at least partially impregnated with the resin. A porous sheet material also facilitates circulation of air through the cured device and evaporation of moisture from beneath the device. This contributes to the patient's comfort and to the maintenance of healthy skin under the device.

Examples of suitable flexible sheet materials include woven or knit fabrics comprised of natural or synthetic fibers such as polyamide, polyester, polyolefin, polyacrylamide, etc. Preferred sheet materials are extensible knit fabrics of fiberglass or polyester. Suitable extensible, heat-set fiberglass fabrics are disclosed in U.S. Pat. No. 4,609,578.

Sheet material used in the support material is generally long, narrow fabric strips (tapes) formed in rolls of various widths, from two inches to six inches wide. The fabric is impregnated with the curable resin material in an amount of about 30 to 80 percent by weight of the support material, and in the preferred embodiment, employing a fiberglass fabric, of from 40 to 60 percent by weight of the impregnated support material. The term "impregnate" is used to describe the condition in which the resin is thoroughly intermingled with and in surrounding relation to the threads or fibers of the fabric and does not necessarily indicate that the resin is to any extent absorbed by the fibers themselves. Generally, the resin solution will flow into the capillary spaces between contiguous filaments of the fabric and will become bonded to the fabric upon curing.

The amount of resinous component applied to the fabric must be sufficient for the formation of a interlayer laminate bond, but not so much as to occlude the porosity and unnecessarily thicken the resin film which should be thin for rapid and complete curing. Excessive resinous component may also cause the support material to be messy to handle due to stickiness or dripping of the resin.

The resin coated fabric strips in roll form are wound on a plastic core and sealed within a moisture and oxygen impermeable package. In the case of moisture-curing resins, the package is opened immediately before use and the roll is fully immersed in tap water for about 5 to 30 seconds. This is sufficient time for water to seep into the porous material and displace air. As long as the resin content is not so high as to cause the openings in the fabric to be filled with resin, more than enough water is absorbed by the roll in this manner. The roll may be squeezed underwater to replace entrapped air with water. When the roll is unwound during wrapping of the material, the excess moisture coats freshly exposed resin surfaces insuring thorough wetting and rapid curing of the material. An alternate method comprises wrapping the material without dipping and then allowing atmospheric moisture or water provided by spraying or by application of a wet towel to cure the prepolymer.

Prior to applying the support material, protective padding is positioned about the limb of the patient. The padding may take the form of a tubular stockinet or some other convenient form, such as for example, an elongated strip or bandage which may be wrapped about the body member.

With the padding in proper position, the moistened support material is wrapped about the limb and over the protective padding in a manner similar to the application of an elastic-type bandage. The material is shaped in a manner similar to the shaping of a rigid synthetic or plaster cast.

Eight or fewer layers of the support material should be sufficient to form a cured device providing adequate support and/or immobilization for most applications. Removal of the cured device can generally be accomplished by applying moderate force to the exposed end of the fabric and delaminating the layers. This is a significant advantage over rigid casts which cannot be easily removed by the wearer and usually require power tools such as a saw for removal. The cured devices of the present invention can also be removed with scissors.

The cured semi-rigid support devices of the present invention are characterized by their flexibility and resiliency as compared to conventional rigid casts formed of synthetic resins or plaster-of-paris. They offer more rigidity however than elastic support bandages and wraps which are not impregnated with a curable resin. They also provide greater support and immobilization.

To measure the degree of immobilization provided by the finished casts of the invention, the following test was devised.

Immobilization Test

The test involves applying a force to a sample of cured support material which has been wrapped around a solid cylindrical-shaped article designed to simulate a body limb. The cured sample is subjected to a bending force at a given rate of speed to a given total deflection.

The solid cylinder used as the simulated limb is made using a urethane hydrogel prepolymer marketed by the AC & S Division of 3M as Chemical Grout 5620 and described in U.S. Pat. No. 4,315,703 as "Prepolymer A"). This material is compounded with clay and water to produce the cylinder. The formulation is as follows:

145 g Chemical Grout 5620
80 g Bentonite Clay (Federal Bentonite, Div. of Aurora Industries, Montgomery, Ill.)
600 g Water The water and clay are premixed, and the prepolymer is added under constant agitation for 10-20 seconds. The mixture is poured into a cylindrical mold which is lined with polyethylene for release. The set time is about 45 seconds from the introduction of the prepolymer into the water. The cylinder has a diameter of 6.0 cm. and a length of 30.5 cm. After curing for 24 hours at 22°-25° C., the cylinder is stored in a moist polyethylene bag and refrigerated to prevent shrinkage.

When water curable support materials are tested, they are immersed as a 4-yard (3.65 m) roll in water for about 20 seconds and wrapped around the cylinder spirally so as to provide a total of four layers over a length of 23-25 cm. of the cylinder. Stockinet is normally used to cover the cylinder before applying the tape.

Support material is applied to a cylinder which has been conditioned at room temperature for 2-4 hours. The support material is allowed to cure for 1 hour at ambient conditions, and the system is replaced in the refrigerator at 2°-5° C. for 18-24 hours before being removed for additional ambient conditioning of 2-4 hours. The test is then performed.

The test equipment is an Instron Tensile Tester Model 1122 set up with a 2-1000 pound (0.9-453 kg) full-scale load cell and a variable speed chart. The cylinder wrapped with the test sample is placed on a sample holder designed specifically to fit into the Instron test equipment to perform a three point bend test. The equipment consists of two parts, a base member and an upper member which are mounted on the Instron. The base member consists of a $\frac{3}{4}$-inch (1.9 cm) aluminum plate 13 inches (33 cm) long and 8$\frac{1}{4}$ inches (20.95 cm) wide. Mounted along the top side of the plate, perpendicular to the lengthwise axis of the plate are two rectangular aluminum supports which are one-inch (2.54 cm) thick, 3 inches (7.62 cm) high and 5$\frac{1}{4}$ inches (13.3 cm) long. The supports are located respectively, 5 inches (12.7 cm) from the ends of the plate, as measured to the center of the support. Each support is mounted 1.5 inches (3.81 cm) from each side edge of the plate. The supports are exactly 3 inches (7.62 cm) apart from each other. Bonded to the top of each support along its length is $\frac{3}{4}$ inch (1.9 cm) diameter aluminum rod stock upon which the test sample is placed. The rods on each support are 3 inches (7.62 cm) apart from center to center. This entire structure serves as the base member providing two points of the three point bend test. The base member is bolted to the base of the Instron and remains stationary during the test. The upper member of the test equipment consists of a one-inch (2.54 cm) thick piece of aluminum which is 5$\frac{1}{4}$ inches (13.3 cm) long by 2$\frac{7}{8}$ inches (7.3 cm) high, i.e., similar in size and shape to the supports on the lower member. A stainless steel cylindrical chuck which is 1$\frac{1}{2}$ inches (3.81 cm) in diameter and 1$\frac{3}{4}$ inches (4.4 cm) high threaded at 13 threads to the inch is fixed to the aluminum piece and is used to mount it onto the Instron. A $\frac{3}{4}$-inch (1.9 cm) diameter aluminum rod 5$\frac{1}{4}$ inches (13.3 cm) long is bonded to the bottom edge of the aluminum piece along its length and provides the third point of contact in the test such that the sample is bent between the two parallel lower supports and the aluminum piece on the upper member, which is also parallel to the lower supports. When fixed to the Instron, the upper member lowers at a given rate of speed and comes in contact with the test sample.

The test sample (which is centered on the simulated limb) is centered on and perpendicular to the two supports of the base member of the test device. The aluminum piece of the top member is allowed to contact the sample at its center at a rate of 1 inch (2.54 cm)/minute to a total deflection of one inch. The settings used on the Instron for full scale load and chart speed are dependent on the rigidity of the particular sample and the sensitivity desired in the measurement, as is known to those skilled in the art.

The test result is taken as that force which results from the resistance imparted by the sample at the maximum deflection point of one-inch. The force reading ("Immobilization Value") is taken directly off the chart.

There is a large difference observed in this test between the Immobilization Values obtained when nonresin-impregnated elastic bandages and rigid-forming cast materials are tested. Generally, the unwrapped support device has an Immobilization Value of about 20 pounds (9 kg). Elastic bandage materials such as an Ace bandage have Immobilization Values of 30-40 pounds (13.6-18.1 kg), depending on the number of rolls. Rigid casts such as those formed from Scotchcast 2 Casting Tape (3M) typically have Immobilization Values in the range of 500-700 pounds (226.5-317.1 kg). In contrast, cured support devices of the present invention have Immobilization Values of 50-400 pounds (22.6-181.2 kg), preferably 80-200 pounds (36.2-90.6 kg).

Resiliency Test

To measure the resiliency of the cured support materials of the present invention, the following Resiliency Test was devised:

The test samples are produced by wrapping the resin-coated tape, which has been activated by water immersion, around a mandrel which has an outside diameter of 5 cm. The mandrel is covered with 2 inch (0.5 cm) stockinet material before wrapping. The sample is wrapped to form six layers of material in a cylindrical shape. The samples are allowed to set at least 24 hours at room temperature before testing.

The test equipment is a Chatillon model USTE tester equipped with a support platen on the bottom and a knife edge platen on the top.

The test is done by measuring the inside diameter of the cured sample followed by placing the sample in the test equipment. The sample is laid lengthwise (parallel to the knife edge) in the tester and the force is applied. The sample is deformed such that the inside surface comes into contact with the opposite wall. The force is removed and the inside diameter is remeasured with a caliper. The percent recovery ("Resiliency Value") is calculated using the two inside diameter measurements.

For rigid casts such as those formed from Scotchcast 2, the Resiliency Value is essentially zero. Rigid casts containing a knit polyester sheet material generally show greater resiliency. Cured support devices of the present invention have a Resiliency Value of at least 80 percent and preferably, 90 to 100 percent.

The invention is further illustrated by the following non-limiting examples.

EXAMPLE 1

To 757.38 g of "Isonate" 143L (UpJohn) were added 1.85 g of benzoyl chloride, 6.6 g of DB-100 (antifoaming agent available from Dow Chemical), 17.80 g of "Ionol" (butylated hydroxytoluene available from Shell Chemical Co.). After allowing these ingredients to mix at ambient temperatures for 10 minutes, 2602.45 g of "Niax" LHT-28 (polyol available from Union Carbide), 112.32 g of "Niax" PPG-425 (polyol available from Union Carbide,) 55.62 g MEMPE (catalyst described in copending application Ser. No. 784,344 filed Oct. 4, 1985), and 145.90 g "Pluronic" F-108 (surfactant available from BASF Wyandotte) were added sequentially. The reaction mixture was heated to 60° C. and held for 3 hours. After cooling, a sample was taken which had a viscosity of 30,000 cps, a measured isocyanate equivalent weight of 1280 grams, an average hydroxy equivalent weight of 1536 grams and an NCO/OH ratio of 2.8.

The resin was coated onto various fabrics including fiberglass, polyester knit, and "Ace" bandage fabric. Each material has a different capacity for resin absorption which necessitated different coating weights to achieve good lamination of the layers in the final cured device. The fiberglass material was 45% resin. The polyester knit was 55%. The "Ace" bandage coating was at 60% resin. All of the samples with the exception of the Ace material were stable. The "Ace" material began to react with the resin very quickly indicating a considerable amount of water present.

EXAMPLE 2

A moisture-curing, silane-based support material was made by dissolving a commercially available reactive liquid silicone rubber compound, Dow Corning "Silastic" 732 RTV, in toluene to 70% solids. The solution was coated onto a 3-inch (7.62 cm) wide fiberglass knit fabric of the type used in "Scotchcast" 2 Casting Tape (3M) described in U.S. Pat. No. 4,609,578 to 45% resin solids and packaged in a moisture impermeable package. After being removed from the package, it was allowed to cure with ambient moisture.

EXAMPLE 3

To 1631.48 g of "Isonate" 143L were added 1.85 g of benzoyl chloride, 6.66 g DB-100, 17.76 g of butylated hydroxytoluene. After allowing these ingredients to mix together at ambient temperature for 10 minutes, 1986 g "Niax" PPG-1025 (polypropylene oxide diol available from Union Carbide) and 55.5 g MEMPE. The reaction mixture was heated to 60° C. and held for 3 hours. After cooling, a sample was taken which had a measured viscosity of 43,000 cps, a measured isocyanate equivalent weight of 544 grams, an average hydroxy equivalent weight of 491 grams and an NCO/OH ratio of 2.8. This material was coated onto knitted fiberglass fabric as described in Example 2 at 45% resin content.

EXAMPLE 4

To 542.85 g of "Isonate" 143L were added 1.85 g of benzoyl chloride, 6.66 g of DB-100, and 17.76 g of butylated hydroxytoluene. The materials were allowed to mix at ambient temperature for 10 minutes. To the mixture were added 3075.38 g of PPG-3025 (a polypropylene oxide diol available from Union Carbide) and 55.5 g of MEMPE. The reaction mixture was heated to 60° C. and held for 3 hours. After cooling, a sample was taken that had a measured viscosity of 38,500 cps, a measured isocyanate equivalent weight of 2325 grams, an average hydroxy equivalent weight of 1550 grams, and an NCO/OH ratio of 1.90. The material was coated onto knitted fiberglass fabric as described in Example 2 at 45% resin content.

EXAMPLE 5

To 314.67 g of Isonate 143L were added 1.75 g of benzoyl chloride, 6.30 g of DB-100 and 16.80 g of "Ionol". After allowing the ingredients to mix at ambient temperature for 10 minutes, 2897.98 g of LHT-28, 210.0 g of "Pluronic" F-108 and 52.5 g of MEMPE were added sequentially. The reaction mixture was heated to 70° C. and held for three hours. After cooling, a sample was taken which had a viscosity of 210,000 cps, an average hydroxy equivalent weight of 2102.89, and a measured isocyanate equivalent weight of 5130 g. The material was coated onto a knitted fiberglass fabric as described in Example 2 at 45% resin content.

EXAMPLE 6

To 724.66 g of "Isonate" 143L were added 1.66 g of benzoyl chloride, 5.94 g of DB-100, and 15.84 g of butylated hydroxytoluene. The materials were allowed to mix at ambient temperature for 10 minutes. To the mixture were added 2247.33 g of PPG-3025 (polypropylene oxide diol available from Union Carbide) and 42.90 g of MEMPE. The reaction mixture was heated to 60° C. and held for 2 hours. At this point 261.69 g of Jeffamine ED-2001 (an amino functional polyoxyethylene ether from Texaco) was added very slowly with good agitation. The reaction was held an additional ½ hour and allowed to cool. The resultant material was a resin having a viscosity of 240,000 cps and a measured isocyanate equivalent weight of 1157 g. The material was coated onto knitted fiberglass fabric as described in Example 2 at 45% resin content.

EXAMPLE 7

To 366.11 g of "Isonate" 143L were added 1.75 g of benzoyl chloride, 6.3 g of DB-100 and 16.80 g of "Ionol". After allowing the ingredients to mix for 10 minutes at ambient temperature, 2848.2 g of LHT-28, 208.33 g of "Pluronic" F-108 and 52.51 g of MEMPE were added sequentially. The reaction mixture was heated to 70° C. and held for 3 hours. After cooling, a sample was taken which had a viscosity of 134,000 cps, an average hydroxy equivalent weight of 2103.84 and a measured isocyanate equivalent weight of 4085 g. The material was coated onto a knitted fiberglass fabric as described in Example 2 at 45% resin content.

The materials of Examples 1–7 were compared with both rigid casts and conventional nonresin-impregnated elastic bandages and wraps of the prior art in the Immobilization and Resiliency Tests described above. The results are given in the following Table I.

TABLE I

| Test Sample | NCO Eq. wt. | Immobilization Value lbs. (kg) | | Resiliency Value |
| --- | --- | --- | --- | --- |
| Control Cylinder | N.A. | 21.5 (9.74 kg) | | N.A. |
| Ace Wrap[1] (1 roll) uncoated | N.A. | 30.0 (13.59 kg) | | 0–5 |
| Dr. Scholl's[2] Tape (5 layers) uncoated | N.A. | 58.0 (26.27 kg) | With Stockinet | 0 |
| | | 62.0 (28.08 kg) | No Stockinet | 0 |
| "Coban" Tape (5 layers) uncoated | N.A. | 42.0 (19.02 kg) | | 0–5 |
| "Scotchcast"[2] Casting Tape | 375 | 549.0 (248.69 kg) | | 0–5 |
| "Scotchcast" Plus Casting Tape | 340 | 628.0 (284.48 kg) | | 0–5 |
| CutterCast ®[3] Casting Tape (3 inch) | Unknown | 165 (74.74 kg) | | 73.0 |
| Example 1 (Fabric as in Example 2) | 1280 | 95.0 (43.03 kg) | | 98.0 |
| Example 2 | | 74.0 (33.52 kg) | | 99.1 |
| Example 3 | 544 | 210.0 (95.13 kg) | | 93.5 |
| Example 4 | 2325 | 70.0 (31.71 kg) | | 91.9 |
| Example 5 | 5069 | 49.0 (22.19 kg) | | 85.0 |
| Example 6 | 1157 | 58.0 (26.27 kg) | | 94.0 |
| Example 7 | 4085 | 64.0 (28.99 kg) | | 93.0 |

[1]"Ace" brand Spandex Elastic Bandage, Bectin Dickinson, 3 inches (7.62 cm) wide and 2 yards (1.82 cm) long (unstretched).
[2]Scholl's Inc., Memphis, Tenn.
[3]Cutter biomedical, Berkeley, California.

What is claimed is:

1. A curable orthopedic support material comprising an elongated strip of flexible sheet material impregnated with a liquid resin system which cures upon exposure to a curing agent, which support material will, when wound at least partially upon itself around a human or animal body part to form a layered cylinder, cure into a resilient semi-rigid support device having an Immobilization Value between about 50 and about 400 pounds (22.6–181.2 kg) and a Resiliency Value of at least about 80 percent; said support material being formed into a roll and packaged as an orthopedic support material with packaging means which prevent contact of the resin with the curing agent prior to use.

2. The support material according to claim 1 wherein said liquid resin system comprises a moisture-curing isocyanate-functional prepolymer formed by the reaction of a polyfunctional active hydrogen-containing component with an excess of polyisocyanate component.

3. The support material according to claim 1 wherein said flexible sheet material is a knitted fabric made of fibers selected from the group consisting of fiberglass, polyolefin, polyamide, polyester and polyaramide or mixtures thereof.

4. The support material according to claim 2 wherein the isocyanate equivalent weight of said resin is between 500 and 5000 grams.

5. The support material according to claim 4 wherein said isocyanate equivalent weight is between 800 and 1200 grams.

6. The support material according to claim 2 wherein said polyfunctional active hydrogen-containing component is a polyol.

7. The support material according to claim 2 wherein said resin has an NCO/OH ratio of 2.2 to 3.8.

8. The support material according to claim 7 wherein said NCO/OH ratio is 2.5 to 3.4.

9. The support material according to claim 6 wherein the average hydroxy equivalent weight of said polyol is at least 400 grams.

10. The support material according to claim 9 wherein the average hydroxy equivalent weight is at least 1000 grams.

11. The support material according to claim 3 wherein said substrate is a fiberglass knit having an extensibility of at least 20 percent in the lengthwise direction.

12. The support material according to claim 1 wherein said resin system further comprises a lubricant to reduce the stickiness of the resin during application to the body.

13. The support material according to claim 12 wherein said lubricant is a surfactant.

14. The support material according to claim 13 wherein said surfactant is a block copolymer of propylene oxide and ethylene oxide.

15. The support material according to claim 2 wherein said resin impregnated substrate is packaged in a moisture proof container.

16. The support material according to claim 1 wherein the cured support device can be removed by applying moderate force to an exposed end of the support material so as to delaminate the layered cylinder and thereby unwrap the cured support device.

17. A cured orthopedic support device formed by curing a curable support material comprising an elongated strip of flexible sheet material impregnated with a liquid resin system by exposure to a curing agent, said device comprising overlapping layers of said support material formed into a cylinder by wrapping around a human or animal body part which cylinder is resilient, semi-rigid and has an Immobilization Value between about 50 and about 400 pounds (22.6–181.2 kg) and a Resiliency Value of at least about 80 percent.

18. The cured orthopedic support device according to claim 17 having an Immobilization Value between 80 and 200 pounds (36.2–90.6 kg) and a Resiliency Value of at least 90 percent.

19. The support device according to claim 17 wherein the cured support device can be removed by applying moderate force to an exposed end of the support material so as to delaminate the layered cylinder and thereby unwrap the cured support device.

20. A method of supporting a human or animal body part comprising the steps of:

providing a curable orthopedic support material comprising a flexible sheet material impregnated with a liquid resin system which cures upon exposure to a curing agent and which, when wound at least partially upon itself around a human or animal body part to form a cylinder, cures into a resilient semi-rigid support device having an Immobilization Value between about 50 and about 400 pounds (22.6–181.2 kg) and a Resiliency Value of at least about 80 percent;

exposing said support material to a curing agent;

wrapping said support material around the human or animal body part in at least partially overlapping layers; and allowing said support material to cure after application to said body part.

21. The method of supporting a body part in accordance with claim 20 wherein said support material is exposed to said curing agent prior to wrapping around the body part by dipping said support material in water.

22. The method of supporting a body part in accordance with claim 20 wherein said support material is exposed to said curing agent after wrapping by contact with atmospheric moisture or water.

23. The method according to claim 20 further comprising the step of removing the cured support device after support of the body part is no longer desired, said removing step comprising applying moderate force to an exposed end of the support material so as to delaminate adjacent layers of the cylinder and thereby unwrap the cured support device.

* * * * *